(12) United States Patent
Kampa et al.

(10) Patent No.: US 7,112,298 B2
(45) Date of Patent: Sep. 26, 2006

(54) METHOD FOR FORMING A MEDICAL DEVICE WITH POLYMER COATED INNER LUMEN

(75) Inventors: Greg J. Kampa, Blaine, MN (US); Pu Zhou, Plymouth, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 100 days.

(21) Appl. No.: 10/264,794

(22) Filed: Oct. 3, 2002

(65) Prior Publication Data

Related U.S. Application Data

(60) Provisional application No. 60/326,861, filed on Oct. 3, 2001.

(51) Int. Cl.
*B29C 41/10* (2006.01)
*B29C 41/14* (2006.01)

(52) U.S. Cl. .................. 264/301; 264/306; 264/307; 427/2.3

(58) Field of Classification Search ........... 264/301, 264/303, 305, 306, 307, 308; 604/523, 524; 427/2.1, 2.25, 2.3
See application file for complete search history.

(56) References Cited

U.S. PATENT DOCUMENTS

| | | | |
|---|---|---|---|
| 3,695,921 A * | 10/1972 | Shepherd et al. | 427/2.28 |
| 3,708,324 A * | 1/1973 | Stebleton | 427/342 |
| 4,636,346 A | 1/1987 | Gold et al. | |
| 4,764,324 A | 8/1988 | Burnham | |
| 4,840,623 A * | 6/1989 | Quackenbush | 604/524 |
| 4,904,431 A | 2/1990 | O'Maleki | |
| 4,954,309 A * | 9/1990 | McGlothlin et al. | 264/307 |
| 5,041,225 A * | 8/1991 | Norman | 210/500.36 |
| 5,049,138 A | 9/1991 | Chevalier et al. | |
| 5,089,205 A * | 2/1992 | Huang et al. | 264/255 |
| 5,472,423 A | 12/1995 | Gronauer | |
| 5,545,708 A * | 8/1996 | Onwunaka et al. | 528/76 |
| 5,601,870 A * | 2/1997 | Haung et al. | 427/133 |
| 5,612,083 A * | 3/1997 | Haung et al. | 264/233 |
| 5,670,111 A * | 9/1997 | Conway et al. | 264/512 |
| 5,702,754 A * | 12/1997 | Zhong | 427/2.12 |
| 5,725,513 A | 3/1998 | Ju et al. | |
| 5,767,189 A * | 6/1998 | Palmer, Jr. | 524/539 |
| 5,817,733 A * | 10/1998 | Rink | 528/71 |
| 5,951,539 A | 9/1999 | Nita et al. | |
| 5,976,995 A * | 11/1999 | Palmer, Jr. | 442/118 |
| 6,042,578 A * | 3/2000 | Dinh et al. | 604/527 |
| 6,048,620 A * | 4/2000 | Zhong | 428/424.4 |
| 6,090,328 A * | 7/2000 | Makuuchi et al. | 264/331.11 |
| 6,159,187 A | 12/2000 | Park et al. | |
| 6,224,803 B1 | 5/2001 | Tiernan | |

(Continued)

FOREIGN PATENT DOCUMENTS

WO  WO 95/29722  11/1995

(Continued)

*Primary Examiner*—Angela Ortiz
(74) *Attorney, Agent, or Firm*—Crompton, Seager & Tufte, LLC (57) ABSTRACT

A medical device, such as a catheter shaft, having an inner lumen defined by a layer of polymer coating, and a method for forming such a medical device. In some embodiments, the method generally includes the steps of applying a polymer coating to an elongated mandrel, and constructing the remainder of the catheter shaft body around the polymer coated mandrel. In some embodiments, the polymer coating layer is made from water dispersible polymer or water soluble polymer.

16 Claims, 5 Drawing Sheets

U.S. PATENT DOCUMENTS

| | | |
|---|---|---|
| 6,242,042 B1 * | 6/2001 | Goldstein et al. ............ 427/2.3 |
| 6,280,545 B1 | 8/2001 | Kanesaka |
| 6,325,790 B1 * | 12/2001 | Trotta ......................... 604/523 |
| 6,347,409 B1 * | 2/2002 | Nile et al. ...................... 2/168 |
| 6,352,666 B1 * | 3/2002 | Nile et al. .................. 264/306 |
| 6,383,434 B1 * | 5/2002 | Conway et al. ............. 264/221 |
| 6,447,835 B1 * | 9/2002 | Wang et al. ................ 427/2.24 |
| 6,479,000 B1 * | 11/2002 | Conway et al. ............. 264/135 |
| 6,569,375 B1 * | 5/2003 | McGlothlin et al. ........ 264/488 |
| 6,613,867 B1 * | 9/2003 | Sonnenschein et al. ....... 528/76 |
| 6,706,313 B1 * | 3/2004 | Goldstein et al. ............ 427/2.3 |
| 2001/0004703 A1 | 6/2001 | Tiernan |
| 2001/0027310 A1 | 10/2001 | Parisi et al. |

FOREIGN PATENT DOCUMENTS

| | | |
|---|---|---|
| WO | WO 97/32623 | 9/1997 |
| WO | WO 00/03756 | 1/2000 |
| WO | WO 01/64259 | 9/2001 |
| WO | WO 02/11806 | 2/2002 |

* cited by examiner

METHOD FOR FORMING A MEDICAL DEVICE WITH POLYMER COATED INNER LUMEN

This application claims priority to U.S. Provisional Patent Application Ser. No. 60/326,861 filed on Oct. 3, 2001.

TECHNICAL FIELD

The invention generally relates to the field of medical devices, and more specifically to medical devices such as intravascular catheters and other diagnostic or therapeutic catheters for use within the body for treatment and diagnosis of diseases. In some embodiments, the invention relates to a catheter shaft design and corresponding methods of manufacture.

BACKGROUND

Intravascular catheters and other diagnostic or therapeutic catheters for use within the body for treatment and diagnosis of diseases are generally known. A number of different catheter structures and methods for making catheters are also known. Each of these different existing structures and methods has certain advantages and disadvantages. There is an ongoing need to provide design alternatives for catheters and alternate methods for producing the catheters.

SUMMARY

The invention relates to a catheter shaft and a method for making a catheter shaft having a polymer coated inner lumen.

Portions of the following detailed description should be read with reference to the drawings, in which like elements in different drawings are numbered identically. The drawings, which are not necessarily to scale, depict selected embodiments and are not intended to limit the scope of the invention. Examples of constructions, materials, dimensions, and manufacturing processes and methods are provided for certain aspects and selected elements. Those skilled in the art will recognize that many of the examples provided have suitable alternatives that may be utilized.

DETAILED DESCRIPTION OF SOME EMBODIMENTS

Some embodiments relate to a medical device, such as a catheter shaft, having an inner lumen defined by an inner layer of polymer coating, and a method for forming such a medical device. In some embodiments, the polymer coating layer is made from a polymer that can be solublized in water, and coated onto a mandrel and cured to form an inner polymer layer. In some other embodiments, the polymer coating layer is made from a polymer that can be dispersed in water, and coated onto a mandrel, and cured to form the inner polymer layer. In some yet some other embodiments, the polymer coating layer is made from a polymer, for example PTFE, polyacrylic acid, and the like, or mixtures thereof, which can be dispersed or solubilized in a non-aqueous solvent.

The method and apparatus described herein can be employed in a broad variety of medical device applications. For example, it is contemplated for use in a broad variety of medical catheters generally, including guide catheters, angioplasty catheters, stent delivery devices, angiographic catheters, neuro catheters, diagnostic catheters, introducer sheaths, other intravascular devices or catheters, biliary catheters, endoscope catheter, and the like. The following sets fourth some example embodiments of guide catheters made in accordance with aspects of the invention, and should be read with reference to the drawings, in which like elements in different drawings are numbered alike.

Figure 1:
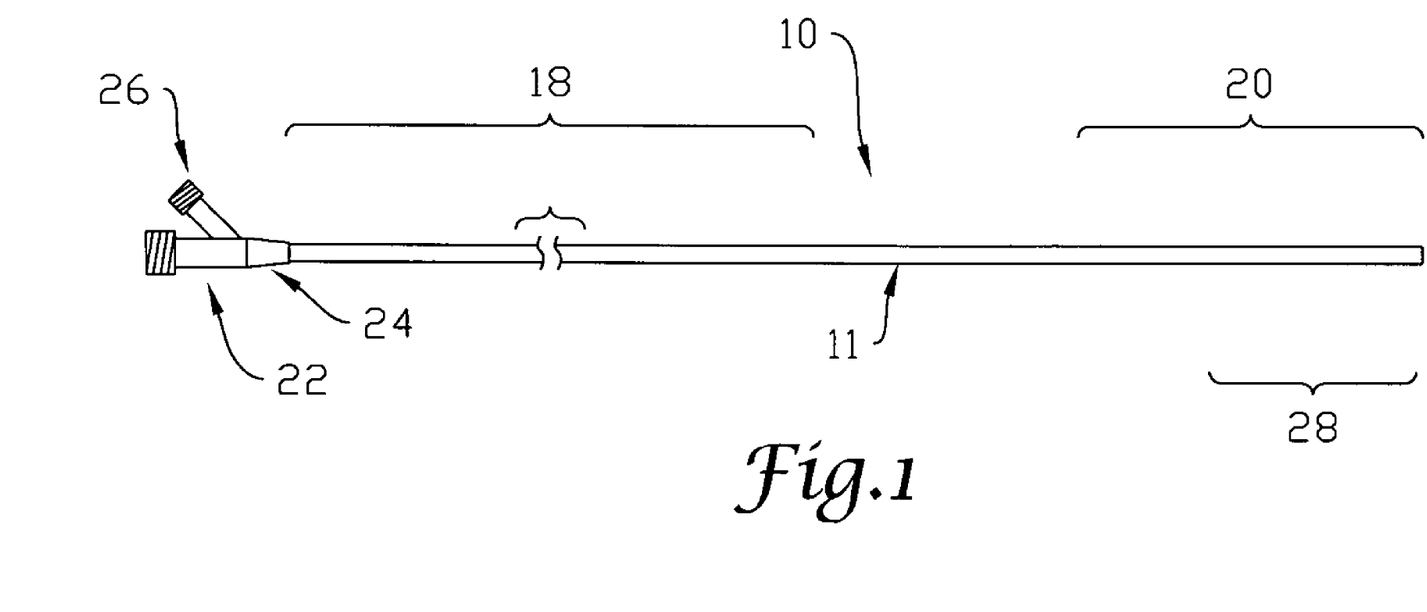
FIG. 1 is a side view of a guide catheter in accordance with one example embodiment.

For example, FIG. 1 shows a sectional side view of a guide catheter 10 including a catheter shaft 11 that is in accordance with one example embodiment of the invention. Guide catheter 10 has a proximal end 18 and a distal end 20. A manifold 22 can be located at the proximal end 18 of the guide catheter. Manifold 22 is connected to catheter shaft 11 and can further include a strain relief 24. The manifold can allow fluid communication with the catheter shaft 11 lumen 13. The manifold 22 can contain ports 26 that allow for fluid-tight connections with the manifold 22 of guide catheter 10. A luer-lock fitting is one example of a fluid-tight fitting that can be attached to the distal end of the manifold ports 26. The manifold 22, and the above-mentioned ports 26, generally allow for the engagement of additional medical devices. For example, guidewires, or other catheters or devices may be inserted through a port 26 on the manifold 22 and further into the inner polymer layer member 12 of the catheter shaft 11. Additionally, fluids, such as diagnostic or therapeutic fluids, may be transmitted through the manifold 22 and into the catheter shaft 11, allowing for their accurate dispersion at the distal end of the guide catheter 20, if so desired.

The distal end of the catheter comprises a distal tip 28. The design of the catheter distal tip 28 can accommodate for movement, for example, through the tortuous vasculature of the human body. Distal tip 28 can be generally comprised of a soft material that minimizes trauma to the surrounding tissue as guide catheter 10 is advanced to, and ultimately engaged with, its final destination within the vasculature. Distal tip 28 can be generally attached to catheter shaft 11 through, for example, thermal processing, or other suitable attachment techniques. The distal tip 28 can be generally processed separately from the catheter shaft 11, and can be modified to meet certain design specifications.

Figure 4:
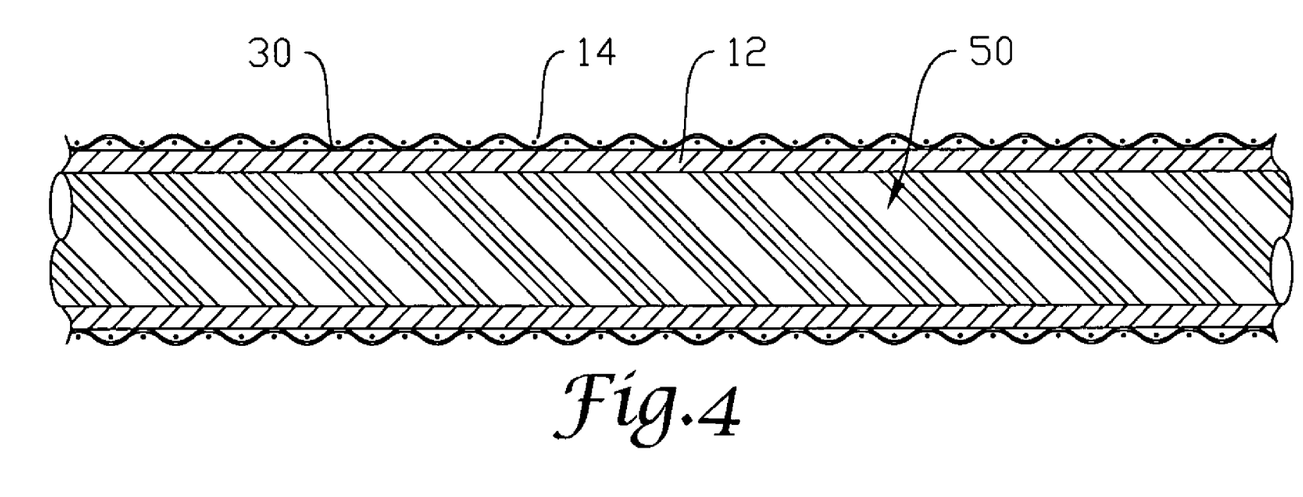
FIG. 4 is a partial cross-sectional side view of the coated mandrel of FIG. 3, further including a reinforcing structure disposed about the outer surface of the coating.
Figure 5:
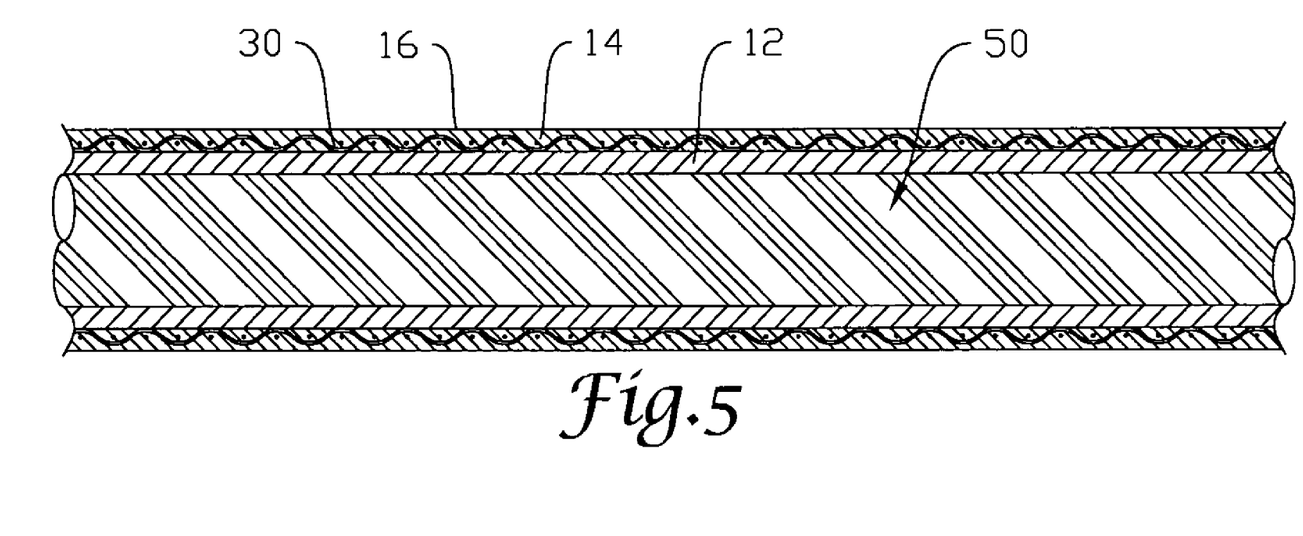
FIG. 5 is a partial cross-sectional side view of the coated mandrel of FIG. 4, further including an outer tubular member or layer disposed about the reinforcing structure.
Figure 6:
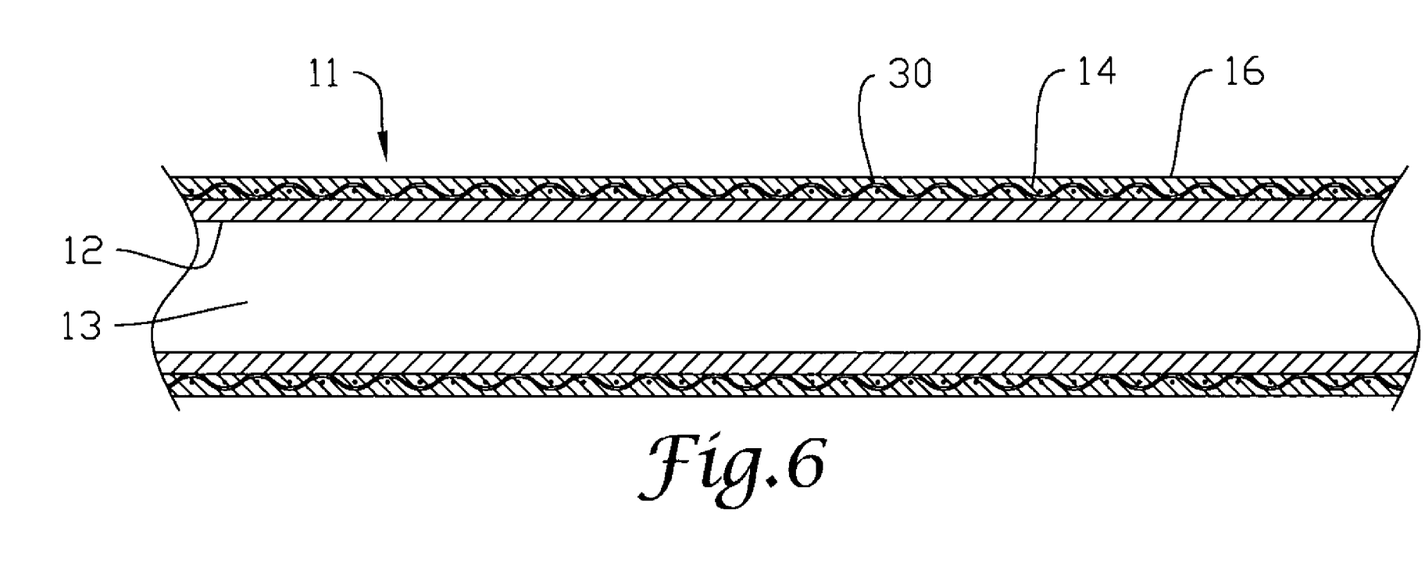
FIG. 6 is a partial cross-sectional side view of the catheter shaft after removal of the mandrel.

FIG. 6 is a partial cross-sectional side view of a portion of a catheter shaft 11 of the catheter of FIG. 1 illustrating some of the structural features of the catheter shaft 11. Catheter shaft 11 is comprised of an inner polymer layer member 12 defining a lumen 13, and that is surrounded by a support member layer 14. An outer tubular member 16 subsequently surrounds support member layer 14. Refer now to FIGS. 2–6 for a discussion of some methods and materials that can be used to construct a catheter shaft 11 in accordance with some embodiments.

Figure 2:
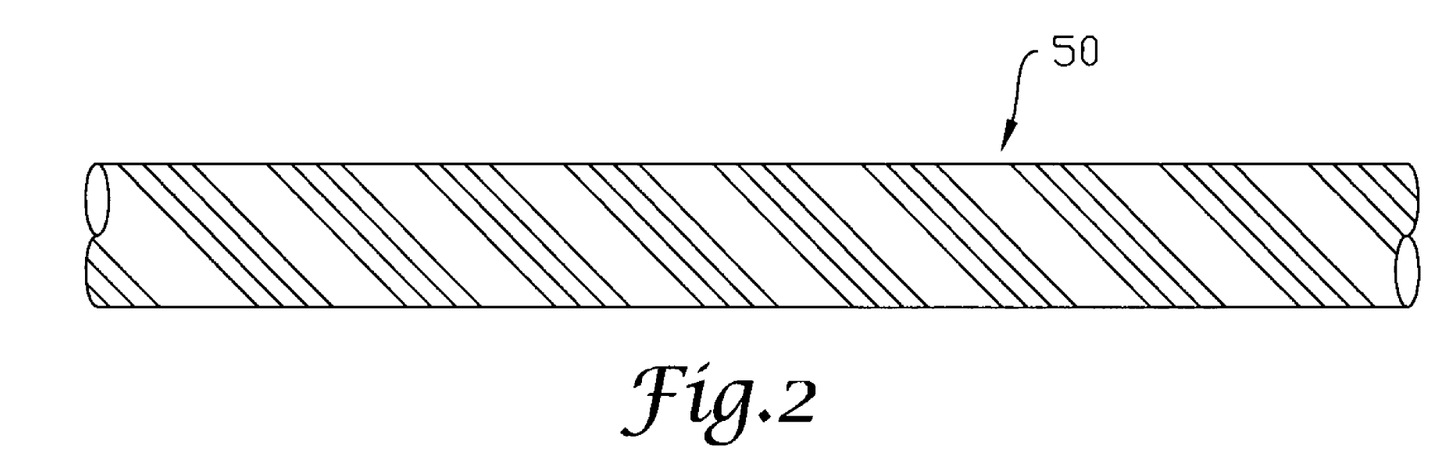
FIG. 2 is a partial cross-sectional side view of a mandrel that can be used in a method of constructing a catheter shaft.

FIG. 2 shows a partial cross sectional side view of a mandrel 50 that can be used in constructing the catheter shaft 11. The mandrel 50 can be any structure that acts as a supporting material for the making of the inner polymer coating layer 12. The mandrel should be sized appropriately and include a geometry so as to provide the desired shape and size of inner lumen in the medical device being constructed. Examples of some structures useful as a mandrel include an appropriately sized, generally elongated, wire, rod, shaft, bar, pole, dowel, strand, or other like structures. Typically, the mandrel is generally circular in cross section, but other geometries are contemplated and would be readily apparent to those of skill in the art and others. For example, in some particular embodiments, the mandrel 50 is a generally circular elongated wire having a diameter en the range of about 0.045 to about 0.115 inches.

The mandrel is generally made of a material that can withstand the environment of the coating process, and can be removed after construction of the coating layer and/or the remainder of the catheter structure. Examples of suitable materials for use in the mandrel include metals, metal alloys, polymer materials, and the like. Some examples of suitable metals and metal alloys include stainless steel, copper, aluminum, silver, brass, nickel, titanium, and the like. Some examples of suitable polymer materials are fluoropolymers, polyacetal, polyester, polyamide, polyacrylates, and the like, or combinations thereof.

In some embodiments, the mandrel is provided with a surface that provides for an enhanced ability to remove the mandrel from the polymer coating layer when desired. For example, the surface of the mandrel can be made of, or coated with, a material having anti-stick properties. For example, in some embodiments, the surface of the mandrel is coated with a material, such as polytetrafluroethylene, to provide an anti-stick surface.

Figure 3:
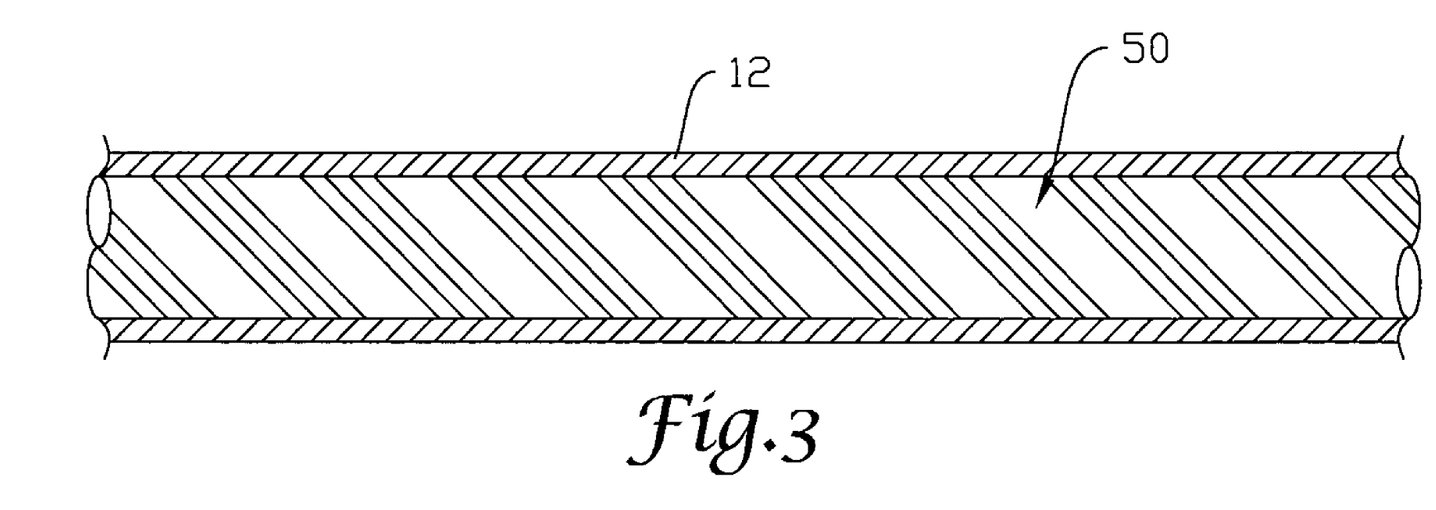
FIG. 3 is a partial cross-sectional side view of the mandrel of FIG. 2 coated with a polymer layer that will become the inner layer of the catheter shaft.

In constructing the catheter shaft 11, the polymer coating layer member 12 can be formed by applying the polymer material over at least a portion of the outer surface of the mandrel 50, as shown in FIG. 3. The finished polymer coating layer 12 can be made of polymer that has the desired characteristics for use as the inner lumen of the particular catheter shaft being constructed. For example, in some embodiments, it is desirable that the inner lumen be defined by a polymer coating material having a low coefficient of friction, or other desirable property.

In some example embodiments, the inner polymer layer member 12 comprises a polymer, for example a water soluble polymer or precursor thereof, that was coated onto a mandrel and appropriately cured or dried to form the inner polymer layer member 12. In some such embodiments, the polymer used to form the inner layer 12, or a precursor of such a polymer, is solubilized in water to form a coating solution. The coating solution is then applied to the mandrel 50 in a suitable manner to provide the desired thickness of the final inner layer 12. As used herein, the terms "water soluble polymer" mean polymers that dissolve completely into water to form a single phase. Some examples of suitable water soluble polymers include: polyvinyl alcohol, polyethyleneoxide, polyethyleneglycol, polyvinylpyrrolidone, carboxymethylcellulose, hydroxyethylcellulose, and the like, and mixtures or combinations thereof.

In some other example embodiments, the inner polymer layer member 12 comprises for example a water dispersible polymer, or precursor thereof, that was coated onto a mandrel and appropriately cured or dried to form the inner polymer layer member 12. In some such embodiments, the polymer used to form the inner layer 12, or a precursor of such a polymer, is dispersed in water to form a coating dispersion. The coating dispersion is then applied to the mandrel 50 in a suitable manner to provide the desired thickness of the final inner layer 12. As used herein, the terms "water dispersible polymer" mean: a water insoluble polymer present as a colloidal particle stabilized by appropriate additives, such as dispersing agents, or self-stabilizing via polar components on the polymer chain. Some examples of water dispersible polymers include styrene-butadiene, acrylate, acrylic polymers, polyester, polyester urethanes, polyacrylamide, and the like, and mixtures thereof.

It is also contemplated that in some embodiments, the inner polymer coating layer will be made of certain polymers, for example PTFE, polyacrylic acid, and the like, or mixtures thereof, which can be dispersed or solubilized in to create a coating solution or dispersion. In some such embodiments, such polymers are dispersed in an aqueous dispersion to create a coating dispersion. However, in other embodiments, such polymers are dispersed or solubilized in an organic solvent, such as xylene, and the like, to create a coating solution or dispersion.

It will also be understood by those of skill in the art and others that a broad variety of additives or modifiers can be used within the polymer material or polymer coating solution or dispersion to enhance or impart desired properties to the final polymer materials. Examples of such additives include reinforcing agents, fillers, antioxidants, inhibitors, thickeners, plasticizers, emulsifiers, colorants, silicas, pigments, carbon black, and the like, and mixtures thereof.

The polymer or polymer solution used to form the inner polymer layer 12 can be coated or applied onto the mandrel 50 using coating or application techniques generally known. For example, the polymer coating can be applied using dip coating, spraying, brushing, extruding, pull coating, or other such techniques. It is contemplated that the coating technique may be done manually or can be automated. The coating technique may call for the coating of mandrels that are generally short elongated members, or, in some instances, the coating of long filaments of elongated mandrel material to create long spools of coated mandrel material.

After the mandrel material is coated with the polymer coating material, the polymer coating material is generally allowed to dry or cure to form the inner polymer coating layer that is generally not water soluble or water dispersible. Primarily, the specific type of polymer or polymer solution used to form the polymer layer determines the appropriate curing or drying process. In some embodiments, the curing process involves simply allowing the polymer layer to cure at room temperature for an appropriate amount of time. Other curing processes may include the use of techniques employing elevated heat, infrared, radio frequency, or the like to enhance or speed up the curing process.

The inner polymer layer can be sized and shaped in accordance with the desired function and use of the final product. As will be apparent, the size and shape of the mandrel will affect the final size and shape of the inner lumen of the inner layer. The following dimensions of the inner polymer layer member 12 are given by way of example only, and are not intended to be limiting. The inner polymer layer member 12 can be generally tubular in shape, and can have a thickness of generally 0.003 inches or less throughout the member's length. In some embodiments, a thickness of generally 0.0015 inches or less, or even a thickness of 0.001 or less can be used. Furthermore, in some embodiments, the inner diameter of inner polymer layer member 12 is from about 0.045 to about 0.115 inches in diameter, depending on desired use.

In some embodiments, the coating or application techniques and the curing techniques can be tailored to provide for the desired thickness or other properties of the inner polymer layer. For example, in some particular embodiments where the inner polymer layer is to be formed of polyvinyl alcohol, and a dip coating technique is used, an aqueous coating solution including in the range of about 5 to about 7% by weight polyvinyl alcohol can be used. In some such embodiments, the mandrel can be dipped into the solution, and withdrawn at a rate in the range about 1 to 3 inches per second. The coated mandrel is than passed through an IR heat zone for drying and/or curing. In some such embodiments, the mandrel can be passed through the IR heat zone once, or a number of times, for example in the range of 1 to 10 times. The speed at which the mandrel is passed through the IR heat zone can also vary, for example in the range of about 0.125 to about 0.5 inches per second. The above parameters given by way of example only, and are not intended to be limiting.

After the inner polymer layer is appropriately formed, and cured, other structural portions of the catheter shaft can be added. For example, FIG. 4 shows a support member layer 14 applied over inner polymer layer member 12. Any appropriate support material or structure generally known can be used, depending upon the desired characteristics of the final device. Those of skill in the art and others will recognize that reinforcing members, such as braids, coils, tubes, wires, fabric, mesh, filaments, and combinations thereof, and other like structures for use as reinforcing structures can be used. The reinforcing member layer 14 can be of any appropriate size, shape, and material for use in the particular medical device into which it will be incorporated. For example, in some embodiments, the reinforcing member layer 12 could have a generally circular, flat, curved, oval, or multisided cross-sectional shape, for example, triangular, square, rectangular, pentagonal, hexagonal, and so fourth.

In some embodiments, support member layer 14 comprises two or more interwoven braided filaments 30 that extend over the length of catheter shaft 11. The braid can be formed using any suitable technique or pattern. In some example embodiments, the patterns and techniques used can include 1 over 1, 2 over 2, 3 over 3, or the like. The braid can be formed using a suitable number of strands or filaments 30. The number of strands or filaments used in such a braided reinforcing member will often depend upon the desired characteristics of the braid, and the patterns or techniques used to form the braid. In some embodiments, the number of strands used can range from 16 to 32, and in some embodiments from 8 to 32. The strands or filaments should be appropriately sized and shaped depending upon the desired characteristics of the braid and pattern used. For example, in some embodiments, the braid is made using braid filaments having a thickness in the range of about 0.00025 to about 0.00225 inches, and in some embodiments, from about 0.0015 to about 0.0020 inches. In some embodiments, the braid is made using braid filaments having a thickness in the range of about 0.0007–00125 inches in height and 0.002–005 inches in width. In some embodiments, the cross-sectional shape of the filaments can be circular, oval, or multisided, for example, triangular, square, rectangular, pentagonal, hexagonal, and so fourth. Furthermore, the braid may include one shape of filament exclusively, or a combination may be utilized.

In some embodiments, the braid can have a braid density of at least about 30 pic, and in some embodiments in the range of about 60 to about 300 pic. In some embodiments, the support member layer 14 has a contoured outer surface resulting from weaving of the filaments 30 to form the braid. The density of the braid can affect the contour surface shape.

Alternatively, support member layer 14 can comprise, for example, at least one non-braided structure, such as a filament or wire extending along at least a portion of the length of catheter shaft 11. This structure may extend along the portion of the shaft in any manner desired to give the final medical device desired characteristics. For example, the structure may extend along the portion of the shaft in a helical fashion about inner polymer layer member 12, for example, in the shape of a coil. Support member layer 14 may additionally be placed in particular locations over the length of the catheter shaft 11 to add rigidity to these particular portions of the catheter shaft. In some embodiments, filaments or wires can be used to construct such a reinforcing structure, and the filaments or wires can generally have dimensions within the range of 0.0007–0.00125 inches in height and 0.002–0.005 inches in width. The filaments or wires can have any desired cross sectional shape, for example, flat, rectangular, square, circular, oval, or other shapes. Furthermore, support member layer 14 may include one shape of filament or wire exclusively, or a combination may be utilized. Filaments or wires used to form support member layer 14 may also be either high or low tensile.

In some embodiments, the support member layer 14 can be prefabricated and then disposed or slid over or onto the inner polymer layer member 12. In other embodiments, the support member layer 14 can be constructed or fabricated directly onto the inner polymer layer member 12. The support material layer may conform to the outer surface of the inner polymer layer. In some embodiments, the support member layer 14 can be constructed or disposed over the inner polymer layer member 12 such that at least a portion of the support member layer 14 is embedded within the inner polymer layer 12. For instance, filaments 30 can be embedded slightly or completely into the inner polymer layer member 12. For example, the filaments 30 may be wrapped around inner polymer layer member 12 at a tension such that the filaments 30 embed slightly or fully into the inner polymer layer member 12. A further process for partially embedding the support member layer 14 into the inner polymer layer member 12 involves heat. In this process, the newly braided catheter is passed through a heat source, such as a heated dye, that can soften the polymer and allow the filaments 30 to partially or totally embed into inner polymer layer member 12 without significantly altering the polymeric structure of inner polymer layer member 12.

Examples of suitable materials for use in constructing the support layer 12, or filaments or wires included therein, can include metals, metal alloys, polymers, and the like. Some particular examples of suitable metals and metal alloys include stainless steel, tungsten, nickel, titanium, nickel-titanium alloy, cobalt, gold, iridium, or the like, or alloys or combinations thereof. Some particular examples of suitable stainless steel alloys include 304 and 440A and 440C stainless steel alloys. In some particular example embodiments, the support member layer 14 is a reinforcing braid adapted and configured for use in an intravascular catheter and is formed with primarily stainless steel filaments. In some embodiments, the support member layer 14 includes combinations of filaments or strands made up of different types of materials. For example, in some particular example embodiments, the support member layer 14 is a reinforcing braid formed with a combination of stainless steel filaments and tungsten filaments. Some examples of suitable polymers include nylon, polyesters, acrylics and combinations of mixtures thereof.

In some embodiments, at least a portion of the support member layer 14 can comprise a radiopaque material, for example, tungsten, platinum, gold, and the like. For example, in a braided support member layer 14, at least one filament 30 forming the support member layer 14 can comprise a radiopaque material. As such, guide catheter 10, or similar medical device comprising at least one radiopaque filament 30, is readily discernable under general fluoroscopic observation, for example, when the device is within the body.

Additional structural layers, such as an outer layer, can also be constructed or disposed on the catheter shaft, and can be used in conjunction with, or in the absence of, a support material layer as discussed above. The material used and the structure of any additional structural layers is dependent upon the desired properties and characteristics of final catheter shaft.

For example, as shown in FIG. 5, one or more outer tubular members 16 can be subsequently formed over support member layer 14. Outer tubular member 16 can be formed, for example, of polymer material applied around the support member layer 14 and inner polymer layer member 12. Such a polymer layer can be applied using application techniques generally known in the art, depending upon the type and characteristics of the particular polymer used. For example, the outer polymer can be applied using dip coating, spraying, brushing, extruding, pull coating, shrink wrapping, heat treatment, or other such techniques.

For example, in some embodiments, the catheter shaft 11 (including the support member layer 14 and inner polymer layer member 12) are passed through an extruder which applies a polymer that flows into the interstitial spaces of support member layer 14 and forms a tubular outer layer 16. In some other embodiments, the outer tube segment or segments made of polymer are slid over the reinforcement layer, and a heat bonding process is used to bond segment or segments of polymer material together and to the catheter shaft. In some embodiments, a heat shrink tube is placed over the outer tube segment or segments, and is preshrunk along some or all of the joints between the outer tube segments. The entire subassembly is then subjected to a heating source for thermal processing. Some examples of suitable heating sources include conductive or convective heat as well as IR, microwave, RF, or other known means of supplying heat. In some embodiments, the entire subassembly is placed in an oven for a specified period of time at a specified temperature to cause the various components of the shaft to thermally bond together. The subassembly is then removed from the oven, allowed to cool, and the heat shrink tube is removed.

Any suitable polymer material for use as an outer layer can be used at the outer tubular member 16, dependent upon the desired characteristics and processing technique. Examples of some suitable materials include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro (propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa. One example of a suitable polyoxymethylene (POM) is Delrin™ commercially available from Dow Chemicals.

Figure 7:
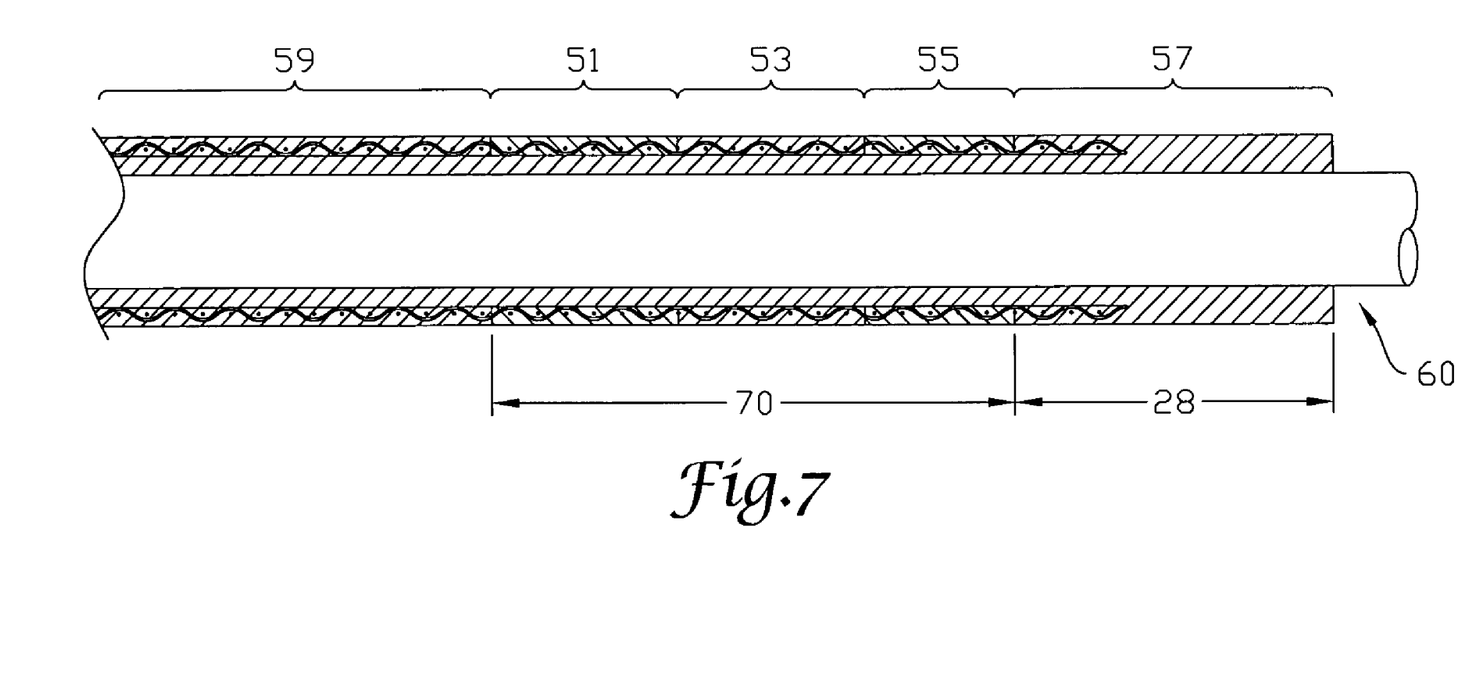
FIG. 7 is a partial cross-sectional side view of the distal portion of another embodiment of a guide catheter shaft, showing different distal segments of the outer tubular member.

As suggested above, in some embodiments, a plurality of outer tube segments made of polymer, often times having different flexibility characteristics. For example, as shown in FIG. 7, in some embodiments, the outer tubular member is made up of a plurality of outer tubular segments, such as a shaft segment 59, a first intermediate segment 51, a second intermediate segment 53, a third intermediate segment 55, and a tip segment 57. Each of the outer tubular segments 59, 51, 53, 55, and 57 is disposed about the support member layer 14, and are generally cylindrical in shape.

When outer tubular member sections are assembled upon the catheter shaft 11, the physical properties, lengths of the individual, or combination of segments, are transferred to the catheter shaft to give a desired flexibility to that region. The physical properties of the inserts, especially flexibility, may be adjusted through varying the materials comprising the segments. Any suitable polymer material can be used for each of the outer tube segments, depending upon the particular flexibility characteristics desired. Typically, the segments of the outer tubular member are manufactured with selected physical properties to give a desired durometer as a measure of flexibility.

For one example, the segments can be comprised of nylon, polyether block amide (PEBA), or a blend of the two. In some embodiments, the PEBA polymer used to form the segments is PEBAX®, available from ATOMCHEM POLYMERS, Birdsboro, Pa. The material of the segments may be blended with a liquid crystal polymer (LCP), for example about 5% LCP. This has been found to enhance torqueability. The tubular segments 59, 51, 53, 55, and 57 can also be made from various performance grades of polyether-ester for example polyether-esters available under the tradename ARNITEL or HYTREL. In order to modify the performance (e.g., flexibility) of the segments, property-enhancing additives may be blended with the PEBA or polyether-ester in order to achieve the desired performance characteristics for the individual segments. Using the various grades of PEBA or polyether-ester, an outer tubular member segments may be created having a durometer on the order of 5–90 D. In preferred applications, segments are on the order of 25–72 D.

In one embodiment, outer tubular segments 51, 53, 55, 57, and 59 can be disposed over the distal portion of the catheter shaft, with each subsequent more distal insert having a lower durometer in order to produce a shaft which continues to become more flexible, distally terminating in a soft distal tip 28. The following is one example embodiment of such a construction.

Referring to FIG. 7, in some particular embodiments, the shaft segment 59 possesses a durometer of about 74 D. The first intermediate tubular segment 51, which is placed so that it abuts the shaft segment 59, possesses a durometer of about 68 D, which is slightly less than that of the shaft segment 59. The second intermediate outer tubular segment 53, which is even more flexible with a durometer of about 55 D, is then positioned over the catheter shaft so that it abuts the first intermediate segment 51. The third intermediate segment 55, having a flexibility of at about 46 D, is then subsequently added to the catheter shaft 70. Finally, the tip segment 57, having a durometer of about 30 D, is added over a portion of the shaft and mandrel 60 so that it abuts the third intermediate segment 55. Because the length of the tip segment 57 is longer than the remaining catheter shaft, the tip segment 57 is also partially displaced over the mandrel 60 as well.

Once the outer tubular segments are properly positioned over the catheter shaft, the catheter 10 goes though a final manufacturing stage. In this stage of manufacturing, a process sleeve, preferably a heat shrink material, is loaded over the outer tubular sections of the catheter shaft 11. These sections are then subjected to a heating source for thermal processing. This heating source can be conductive or convective heat as well as IR, microwave, RF, or other known means of supplying heat. The temperature from the heating source causes the outer tubular member materials to flow sufficiently to adherer to the shaft and to each other, with the inside surface conforming to the contour surface of the support member layer 14. The tip outer tubular segment 57 additionally flows over the mandrel 60 creating a distal tip 28 that covers the exposed distal end of the catheter shaft. Once cooled, the process sleeve is removed. Furthermore, the mandrel 60 is withdrawn. The result is a modified distal section with a soft distal tip 28.

After the catheter shaft 11 is assembled in an appropriate manner, the mandrel 50 is then removed to expose the inner lumen of the catheter shaft, which is defined by the inner polymer coating layer 12. For example, both FIG. 6 shows partial cross-sectional view of catheter shafts with the mandrel removed. In some embodiments, the mandrel 50 is made of an easily deformable material, such as copper, and the like, such that the mandrel can be removed by applying a lateral force on both ends of the mandrel such that the mandrel deforms, and can be removed. In some other embodiments, however, the mandrel 50 is made of a relatively non-deformable material, such as stainless steel, and is therefore pulled in one direction and slid out of the lumen without significant deformation.

EXAMPLES

The following examples are intended to exemplify embodiments of the invention, and is to be construed as a limitation thereof.

Example 1

This example explains the process used to manufacture a 6 french guide catheter containing an inner lumen defined by a polymer coating layer comprising polyvinyl alcohol (PVA). The catheter was produced using the following steps:

1.1 A fresh 4% aqueous solution of PVA was formulated by admixing 200 ml of distilled water and 12 grams of PVA solid, and applying heat (170° F.) and a mechanical stirring motion until the solution turns clear.

1.2 The clear solution of PVA was then poured into an appropriately sized dipping fixture until the fixture was completely full.

1.3 A 48-inch, smooth mandrel (stainless steel 304V) coated with polytetrafluroethylene (PTFE) was obtained for used as the core mandrel material. The mandrel was wiped clean with a cloth dampened with isopropyl alcohol (IPA), and skin contact with any area to be coated or that was coated was avoided.

1.4 In a vertical orientation, the mandrel was carefully lowered into the fresh PVA solution in the dipping fixture until 44" of the mandrel is submersed.

1.5 The mandrel was then slowly extracted from the solution at a constant rate, while avoiding contact of the mandrel with the walls of the dipping fixture. The mandrel then had an uncured PVA coating thereon.

1.6 The PVA coated mandrel was hung vertically on a rack so that there was no contact on the PVA coated portions of the mandrel. The mandrel was allowed to hang freely to dry and cure the PVA coating at room temperature for two hours.

1.7 Steps 1.4–1.6 were then repeated three additional times to the same mandrel to build up the PVA coating.

1.8 After the PVA coating was dried, the PVA coating was heat treated to drive off water molecules that vaporize. This was done by placing the PVA coated mandrel into a convection tube oven at 495° F. for 60 seconds.

1.9 An appropriate prefabricated reinforcement braid was then provided, and cut to the correct length to encompass the entire length of the prepared mandrel. The prefabricated braid came with an acetyl core. The acetyl core was partially removed from the distal end of the braid, and the distal end of the braid was annealed. The acetyl core was then completely removed from within the braid, and the braid was placed over the PVA coated mandrel.

1.10 Once the braid was disposed around the PVA coated mandrel, the distal end of the braid was twisted adjacent the distal end of the coated mandrel such that the distal end of the braid was maintained on the distal end of the mandrel. The braid was then stretched from the distal to the proximal end, and the proximal end of the braid was twisted onto the proximal end of the PVA coated mandrel.

1.11 The distal outer tubular segments with the proper length and durometer, were then loaded over the braid and mandrel from the distal end in appropriate order. In this case, four distal outer tubular segments were used, including a distal tip segment, and three intermediate segments. The distal tip segment was placed on the distal portion of the catheter within the proper annealed braid portion. A distal stop was placed on the distal end of mandrel and heat shrunk into place. The tip segment was then butted up to the distal stop, and each sequential intermediate segment was butted up to the next distal segment.

1.12 The shaft segment was then cut to the appropriate length, and slid over the braid from proximal end of mandrel unit it butted up to the last intermediate distal segment.

1.13 A stop was then placed on the proximal end of mandrel up against shaft segment and heat shrunk into place.

1.14 Place the entire shaft into a FEP shrink tube of the proper dimensions. The heat shrink tube was preshrunk along some or all of the joints between the outer tube segments.

1.15 Conditions of manufactures tube oven were set to 90 sec and 495° F., while allowing time for the oven to maintain constant temperature. The shaft was placed into the fixture, with tip up, and the start button on the re-flow oven apparatus was pressed.

1.16 After the re-flow process was complete, the part was allowed to cool at room temperature. Once cool, the FEP shrink tube was skived and removed.

1.17 The mandrel was then extracted from the guide catheter just formed. Thus leaving a guide catheter shaft with a lubricious inner lumen and an overall thin wall.

1.18 The mandrel can be reused until there is noticeable physical damage to the smooth PTFE coating.

1.19 The catheter shaft continues onto the tip bonding process.

Example 2

This example explains the process used to manufacture a 6 french guide catheter containing an inner lumen defined by a polymer coating layer comprising polyvinyl alcohol (PVA). The catheter was produced using the following steps:

2.1 A fresh 4% PVA solution was formulated by applying heat and a mechanical stirring motion to 700 Grams D.I. water and 28 grams PVA solid until the solution turns clear, using an automatic mixer.

2.2 The clear solution was poured into a dipping tank fixture until the fixture was completely full.

2.3 A dipper control panel was set at a speed of 2 in and speed of 2 out, with no dwell time.

2.4 A 48-inch smooth Teflon coated mandrel was obtained, and wiped with a cloth dampened with IPA while avoiding any skin contact with any area to be coated or that is coated.

2.5 The mandrel was attached in the vertical orientation to the dipper, and aligned with the dipping tank fixture. The dipper was activated, while making sure the mandrel was not rubbing against the walls of the fixture.

2.6 When the cycle was complete, the mandrel was hung vertically on a rack so that there is no contact on the coated portions of the mandrel. The mandrel was allowed to hang freely to cure at room temperature for one hour.

2.7 Steps 2.4 through 2.6 were repeated three additional times.

2.8 After coating was dried, the PVA was heat treated to drive off water molecules that vaporized by placing the mandrel into a manufacturing tube oven at 495° F. for 30 seconds.

2.9 An appropriate prefabricated braid was cut to the correct length to encompass the entire length of the mandrel. An acetel core present in the prefabricated braid was partially removed from the distal end of the braid, and the distal end of the braid was annealed. The acetel core was then completely removed, and the braid was loaded over the mandrel with PVA coating.

2.10 The distal end of braid was twisted, and the braid was stretched from distal to proximal end. The proximal end of the braid was then twisted.

2.11 Polymer outer tubular segments and tip segment, with the proper lengths and durometers, were then loaded over the braid and mandrel from the distal end. The distal reinforced tip segment was placed on the distal portion of the catheter within the proper annealed braid portion. A distal stop was placed on the distal end of mandrel and heat shrunk. The tip and outer tubular segments segment were butted up to the distal stop.

2.12 The tubular shaft segment, which was cut to appropriate length, was slid over the braid from the proximal end of mandrel unit it butted up to the distal tubular segment.

2.13 A stop was placed on the proximal end of mandrel up against the shaft segment and heat shrink.

2.14 The mandrel with the braid, PVA coating and outer tubular polymer materials was inserted into a FEP shrink tube of the proper dimensions.

2.15 The conditions of a re-flow oven apparatus were set to 210 seconds and 495° F. Time was allowed for the oven to maintain constant temperature. The mandrel with the braid, PVA coating and outer tubular polymer materials was placed into the fixture, with the tip up, and the re-flow oven apparatus was started.

2.16 After the re-flow process was complete, the mandrel with the braid, PVA coating and outer tubular polymer materials was allowed to cool at room temperature. Once cool, the FEP shrink tube was skived and removed.

2.17 The mandrel was then extracted from the guide catheter just formed. Thus leaving a guide catheter shaft with an inner lumen and an overall thin wall. The mandrel can be reused until there is noticeable physical damage to the smooth Teflon coating.

2.18 The catheter shaft was then further processed for incorporation into a final guide catheter. For example, the catheter goes through a tip bonding process, is cut to length, the shaft is flared, and a hub is molded onto the proximal end.

Example 3

In this example, a series of test were run to test some examples parameters for coating a mandrel with polyvinyl alcohol (PVA) for use as an inner layer for a catheter shaft. The variables tested in this example include the solution concentration of PVA, the withdrawal rated from the PVA solution during dipping, the number of dips into the solution, and the withdrawal rates from an IR heating zone. The solution concentrations used were in the range of 5 to 7% by weight of the solution, the withdrawal rates from dipping in the solution ranged from 1 to 3 inches per second, and the withdrawal rates from the IR heating zone range from 0.125 to 0.5 inches per second.

During this example, nine Rothgreaves DR-55 coated mandrels with a finished outer diameter of about 0.074 inches were used. The PVA solutions used were created from DuPont's Elvanol, a polyvinyl alcohol powder grade 71-30. A Surface Modification Project dipper apparatus was used to dip the mandrels into the PVA solutions, and to move the dipped mandrels through the IR field.

The following parameters were held constant: temperature of the IR heat zone has held at approximately 190° F.; the viscosity of the solutions were held generally constant; the drying cycles began with the arm inserting the mandrel into the IR zone at 3 inches per second, and withdrawn at the given variable rates.

The output measurement made include the number of cycles through the IR heat zone that were needed, the average thickness of the coating, the coating thickness uniformity throughout the length of the coating, and the thickness uniformity around the circumference.

The results indicated that the concentration of the solution and the rate of withdrawal through the IR heat zone had a slightly larger affect on the coating thickness than the rate of withdrawal from the coating solution. It was determined that for better coating thickness in this example, the concentration levels of PVA, and the withdrawal rate through the IR heat zone should in the higher levels. Also, increasing the concentration level of PVA was found to increase the level of variability in the average thickness, while, to a lesser extent, increasing the withdrawal rate through the IR heat zone decreases variability in the average thickness.

The results also indicated that the withdrawal rate through the IR had the greatest effect of the parameters tested on the number of IR cure passes required. Faster speeds required more passes. Additionally, withdrawal rates through the PVA coating solution may reduce the variation in the number of IR passes needed, while slower withdrawal rates through the IR heat zone may reduce the variations in the number of IR cure passes needed. It was also determined that in at least some embodiments wherein a coating thickness of about 10.5μ is desired, a PVA concentration of 7%, a withdrawal rate from the PVA solution of about 1 inch per second, and a withdrawal rate of about 0.5 inches per second may be desired.

Example 4

This example explains the process used to manufacture a catheter shaft containing an inner lumen defined by a polymer coating layer comprising polytetrafluroethylene (PTFE). The catheter shaft was produced using the following steps:
1. A water-based PTFE dispersion was obtained. The particular formulation used in a PTFE coating dispersion commercially available from Boyd Coating Research Co. Inc. The coating dispersion was formulated to minimize adhesion of the coating dispersion to the mandrel surface.
2. A thin layer of the coating dispersion, for example 0.0003 inches in thickness, was sprayed onto a stainless steel 304 mandrel.
3. The coating was cured in an oven at 750° F. for five minutes.
4. An appropriately sized 2/4 tungsten and stainless steel 304 hybrid 85 Pic braid was then loaded over the coated mandrel. The 2/4 means 2 of 2 mil round wire (one is Tungsten wire, another is high tensile stainless steel 304 wire) and 4 of 1 mil high tensile stainless steel 304 round wire.
5. PBT/Arnitel polymer blend outer polymer tubes with section dimensions similar to those discussed in reference to FIG. 7 were then loaded over the braid. Specifically, the polymer tubes included a PBT/Arnitel 74D 60/40 blend as a shaft tube material, followed by a tube made form a PBT/Arnitel 74D 30/70 blend material, followed by a tube made of an Arnitel 55D material, which was then followed by a tube made of an Arnitel 40D material as the tip.
6. A FEP shrink tube was then loaded over the polymer tubes.
7. The unit of item 6 was then heated at 480F for two minutes in a tube oven to reflow.
8. After the re-flow process was complete, the mandrel with the braid, PTFE coating and outer tubular polymer materials was allowed to cool at room temperature. Once cool, the FEP shrink tube was skived and removed.
9. The mandrel was then extracted from the guide catheter shaft just formed, thus leaving a guide catheter shaft with a lubricious inner lumen and an overall thin wall. To remove the mandrel, the distal half inch of the polymer tube was cut off, to expose the mandrel. The exposed mandrel portion is then inserted through an opening in a structure that is just large enough for the mandrel, but that will not allow the unexposed portion of the unit to pass though. The exposed mandrel was pulled by hand through the hole, and the mandrel will be removed from the guide catheter shaft. The mandrel can be reused until there is noticeable physical damage to the outer surface.

Those skilled in the art will recognize that the present invention may be manifested in a wide variety of forms other than the specific embodiments contemplated and described herein. Accordingly, departures in form and detail may be made without departing from the scope and spirit of the present invention as described in the appended claims.

What is claimed is:

1. A method for forming a medical device comprising:
providing an elongated mandrel;
providing an aqueous coating solution including water and a water soluble polymer dissolved in the water wherein the water soluble polymer comprises polyvinyl alcohol, polyethyleneoxide, polyethyleneglycol, polyvinylpyrrolidone, carboxymethylcellulose, hydroxyethylcellulose, or mixtures thereof;
applying the aqueous coating solution to the elongated mandrel to define a polymer coating layer on the mandrel, wherein the polymer coating layer is a generally continuous layer of the water soluble polymer, and wherein the generally continuous polymer coating layer comprises the water soluble polymer that is water soluble or water dispersible prior to curing, and is not water soluble after curing;
disposing at least one additional layer around a portion of the polymer coating layer, wherein the one additional layer includes a reinforcing layer; and
removing the elongated mandrel to expose an inner lumen at least partially defined by the polymer coating layer.

2. The method of claim 1, wherein the polymer coating layer comprises polytetrafluroethylene, polytetrafluoroehylene, polyacrylic acid, or mixtures thereof.

3. The method of claim 1, wherein after the applying step, the polymer coating layer is cured.

4. The method of claim 1, wherein after the applying step, the polymer coating layer is heat treated.

5. The method of claim 1, wherein the aqueous coating solution is applied to the elongated mandrel through dip coating.

6. The method of claim 1, wherein the aqueous coating solution is applied to the elongated mandrel through extrusion.

7. The method of claim 1, wherein the polymer coating layer has a thickness in the range of about 0.0005 and about 0.005 of an inch.

8. The method of claim 1, wherein the polymer coating layer has a thickness in the range of about 0.001 and about 0.003 of an inch.

9. The method of claim 1, a wherein the reinforcing layer comprises one or more elongated filaments.

10. The method of claim 1, wherein the reinforcing layer includes a braid.

11. The method of claim 1, wherein the reinforcing layer includes a coil.

12. A method for forming a catheter shalt having a polymer coated inner lumen, the method comprising:
providing an aqueous coating solution including water and a water soluble polymer dissolved in the water wherein the water soluble polymer comprises polyvinyl alcohol, polyethyleneoxide, polyethyleneglycol, polyvinylpyrrolidone, carboxymethylcellulose, hydroxyethylcellulose, or mixtures thereof;

applying the aqueous coating solution to an elongated mandrel to define a polymer coating, wherein the polymer coating is a generally continuous layer of the water soluble polymer;

disposing a reinforcement material around the mandrel and onto the polymer coating;

disposing at least one outer member over the reinforcement material and polymer coating; and removing the mandrel from the polymer material to expose the polymer coated inner lumen.

13. A method for fanning a catheter shaft having a polymer coated inner lumen, the method comprising:

providing an aqueous fluid comprising a water soluble polymer composition dissolved in water, wherein the polymer composition consists essentially of polyvinyl alcohol, polyethyleneoxide, polyethyleneglycol, polyvinylpyrrolidone, carboxymethylcellulose, hydroxyethylcellulose, or mixtures thereof, and wherein the water soluble polymer composition is the sole polymer component within the aqueous fluid;

applying the aqueous fluid to an elongated mandrel to define a polymer coating;

disposing a reinforcement material around the mandrel and onto the polymer coating;

disposing at least one outer member over the reinforcement material and polymer coating; and removing the mandrel from the polymer material to expose the polymer coated inner lumen.

14. The method of claim 1, wherein the coating solution further includes one or more additives or modifiers.

15. The method of claim 13, wherein the aqueous fluid further includes one or more additives or modifiers.

16. The method of claim 12, wherein the coating solution further includes one or more additives or modifiers.

* * * * *

UNITED STATES PATENT AND TRADEMARK OFFICE
CERTIFICATE OF CORRECTION

| | | |
|---|---|---|
| PATENT NO. | : 7,112,298 B2 | Page 1 of 1 |
| APPLICATION NO. | : 10/264794 | |
| DATED | : September 26, 2006 | |
| INVENTOR(S) | : Greg J. Kampa et al. | |

It is certified that error appears in the above-identified patent and that said Letters Patent is hereby corrected as shown below:

Column 5
Line 63, delete "0.0007-00125", and insert therefor -- 0.0007-0.00125 --.

Line 64, delete "0.002-005", and insert therefor -- 0.002-0.005 --.

Column 14
Line 60, delete "shalt", and insert therefor -- shaft --.

Column 15
Line 11, delete "fanning", and insert therefor -- forming --.

Signed and Sealed this

Nineteenth Day of December, 2006

JON W. DUDAS
*Director of the United States Patent and Trademark Office*